United States Patent [19]

Scherf

[11] 4,118,565

[45] Oct. 3, 1978

[54] ACETALS OF GLYOXAL AND TEREPHTHALDEHYDE

[75] Inventor: Gerhard Wolfgang Helmut Scherf, Dundas, Canada

[73] Assignee: Canadian D. A. Stuart Oil Co. Limited, Scarborough, Canada

[21] Appl. No.: 759,189

[22] Filed: Jan. 13, 1977

Related U.S. Application Data

[62] Division of Ser. No. 640,273, Dec. 12, 1975, abandoned.

[51] Int. Cl.$^2$ .................. C07D 295/08; C07C 43/30
[52] U.S. Cl. .................. 544/87; 544/174; 260/615 A; 260/611 A; 260/611 B
[58] Field of Search .......... 260/247.7 Y, 246 B, 260/615 A, 611 B, 611 A; 544/87, 174

[56] References Cited

U.S. PATENT DOCUMENTS

| | | | |
|---|---|---|---|
| 2,397,514 | 4/1946 | Staff | 206/615A |
| 2,885,443 | 5/1959 | Kress | 260/615 A |
| 2,902,470 | 9/1959 | Kress | 260/615 A |
| 2,905,719 | 9/1959 | de Benneville et al. | 260/615 A |
| 2,905,720 | 9/1959 | de Benneville et al. | 260/615 A |
| 2,905,721 | 9/1959 | de Benneville et al. | 260/615 A |

*Primary Examiner*—Jose Tovar
*Attorney, Agent, or Firm*—Neuman, Williams, Anderson & Olson

[57] ABSTRACT

A surface active compound comprises at least one lipophilic group and at least one hydrophilic oxyethylated group linked together through acetal linkages so that, on acidification of an aqueous medium containing such a surface active compound, rupture of such acetal linkages permits separation of said lipophilic group, possibly with lipid material associated therewith, from the aqueous medium in which the oxyethylated groups remain so in turn permitting recovery of such lipophilic groups and any such lipid material, and effective elimination of active surface active compound from the aqueous phase.

4 Claims, No Drawings

ACETALS OF GLYOXAL AND TEREPHTHALDEHYDE

REFERENCE TO PRIOR APPLICATION

This application is a division of application Ser. No. 640,273, filed Dec. 12, 1975, now abandoned.

BACKGROUND OF THE INVENTION

The present invention relates to surface active compounds, their preparation and their use, and more particularly to surface active compounds which can have their structures readily modified to permit not only the separation and recovery of lipid material from an aqueous medium in which such compounds are used but also to provide, after such separation, an aqueous phase in which the contents of such lipid material and of active surface active material are substantially reduced.

A variety of surface active agents or compounds are well known and such compounds are used for a variety of purposes. Merely by way of example, there can be mentioned the uses of such compounds in household detergents and other cleaning compositions and in industrial products such as detergents, emulsifying agents, wetting agents, coupling agents and substantive agents as used in fabric treatment. Surface active compounds are generally used in aqueous media and it is fully recognized that the disposal of large quantities of waste waters containing surface active compounds presents numerous problems in sewage treatment plants and in natural bodies of water such as rivers and lakes into which such waste waters frequently find their way.

All surface active compounds have a molecular structure which comprises a lipophilic or hydrophobic portion or moiety bonded to a hydrophilic portion or moiety. It is believed that, in the use of a surface active compound in an aqueous medium, the hydrophilic portions of the molecules effectively become attached to water molecules so effectively providing dissolution of the compound in the aqueous medium. It is also believed that the lipophilic portions of such molecules become attached to any lipidic material which is present so as effectively to maintain that material in dispersion in the aqueous phase. For example, in the use of a household detergent, the lipophilic portions of the surface active compound molecules become associated with oil, grease or dirt molecules with the result that such molecules effectively become dissolved or at least dispersed in the aqueous phase. Since an excess of detergent will often be used, that aqueous phase will normally also contain molecules of the surface active compound with which no lipid molecules are associated. The principal problem which arises with such use of detergents is a result of the presence in the waste water of the surface active compound regardless of whether or not the molecules thereof have any lipid molecules associated therewith.

On the other hand, in the use, for example, of a surface active compound as an emulsifying agent to form an aqueous emulsion of an industrial cutting oil, the association with the molecules of the surface active compound of molecules of both water and the lipid material (i.e. the cutting oil) provides a stable emulsion which, if discarded after use into a waste water system, results not only in serious pollution of the waste water with both the surface active compound and the cutting oil but also to a significant loss of the valuable cutting oil itself.

Presently known surface active compounds fall, as is well known, into four classes, namely anionic, cationic, amphoteric and non-ionic which differ essentially in the manner in which their hydrophilic portions effectively associate with water molecules.

As hereinbefore indicated, the problems involved in the disposal of waste waters containing surface active compounds and lipid materials dispersed in such waters are fully recognized and attempts have heretofore been made to treat such waste waters to separate such surface active compounds and lipid materials from such waters. Some success has been attained in the purification of waste waters containing anionic and cationic surface active compounds by treating such waste waters with flocculating agents so as to rupture the so-called bonds between the hydrophilic moieties of the surface active compounds and the water molecules so as then to allow separation of a lipid phase and/or the surface active compound from the aqueous phase. Various adsorption processes have also been suggested for purifying waste waters containing surface active compounds and lipid materials. It has also been suggested to provide biodegradable surface active compounds which can be destroyed by certain bacteria.

The known processes for the deactivation and/or removal of surface active compounds from waste waters have, however, presented various problems. For example, the previously proposed adsorption processes are relatively slow and, for the treatment of large quantities of waste waters, call for substantial capital investment. Additionally, if it is then desired to recover the lipid material, it is then necessary to recover that material from the adsorbent at further expense.

Additionally, many of the previously proposed processes are not effective for deactivating non-ionic surface active compounds and consequently very substantial volumes of waste waters containing such compounds and lipid materials associated therewith are discarded each year into sewage plants and natural bodies of water. Additionally, the use of non-ionic surface active compounds is precluded in many applications in view of the difficulty of purifying waste waters containing such compounds.

It is a principal object of the present invention to provide a surface active compound which can readily be deactivated when present in waste waters so as then also to permit the ready removal from such waters of lipid material previously dispersed therein and to reduce the amount of active surface active compound which remains in the waste waters which are to be discarded.

It is a further object of this invention, in accordance with a preferred feature thereof, to provide an improved and de-activatable surface active compound.

Other objects of the invention will become apparent as the description herein proceeds.

SUMMARY OF THE INVENTION

A surface active compound in accordance with the present invention comprises, as do known surface active compounds, a molecular structure which comprises a lipophilic moiety or portion and chemically bonded to that lipophilic moiety a hydrophilic moiety. In distinction to known surface active compounds, those of the present invention include a bridging segment interconnecting the hydrophilic and lipophilic moieties and which incorporates a normally stable linkage which is, however, ruptured when such a surface active compound is exposed to a predetermined condition when dispersed in an aqueous medium. In the use of such surface active compounds under conditions other than such predetermined condition, the surface active compound functions in a normal manner. If, however, such a surface active compound present in an aqueous medium is subsequently exposed to such a predetermined condition, the rupture of the aforesaid linkage in the bridging segment permits separation of the lipophilic and hydrophilic moieties so as to provide two distinct phases. It will further be understood that, after such separation, the resulting aqueous phase will contain the hydrophilic moieties of the surface active compound while the lipidic phase will contain the lipophilic moieties of the surface active compound as well as any lipid material which was associated with those lipophilic moieties.

The present invention embraces surface active compounds in which hydrophilic and lipophilic moieties are interconnected by bridging segments incorporating normally stable linkages which rupture when such compound dispersed in an aqueous medium is acidified.

The compounds of the present invention are those which correspond to the formula:

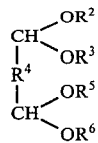

in which at least one of $R^2$, $R^3$, $R^4$, $R^5$ and $R^6$ represents a hydrophilic moiety and in which at least one of $R^2$, $R^3$, $R^4$, $R^5$ and $R^6$ represents a lipophilic moiety.

Although this invention is not restricted to surface active compounds in which the lipophilic and hydrophilic moieties are of any particular structure, there may be mentioned merely for the sake of illustrating this invention particular structures for such moieties which have in practice proven to be highly effective. For example, the lipophilic moieties in surface active compounds in accordance with this invention are usefully straight and branched chain hydrocarbon groups having from 8 to 24 carbon atoms and more usually from 10 to 18 carbon atoms. Typical of such groups are stearyl and myristyl groups. Other especially suitable lipophilic moieties are aklylated aromatic groups particularly those having from 6 to 18 carbon atoms in their alkyl group.

Typical hydrophilic moieties for use in non-ionic surface active compounds in accordance with the present invention are hydrophilic oxyalkylated groups and especially oxyethylated groups containing from 1 to 24 oxyethylene groups. Typical preferred hydrophilic groups are as follows:

a. oxyethylated methyl groups

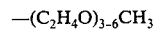

b. oxyethylated n-butyl groups

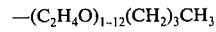

c. oxyethylated N-morpholine groups

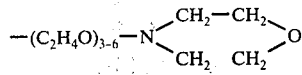

The surface active compounds of this invention can be prepared by any appropriate procedure. For example, they can be prepared by the condensation of a polyaldehyde with a plurality of alcohols.

Such condensation reactions can be carried out in the presence of an acidic catalyst at an elevated temperature and in a suitable solvent such as benzene to permit separation of the water by azeotropic distillation. After completion of the condensation reaction, the acid catalyst will be neutralized so that the products can be used in aqueous media without undesired rupture of the acetal linkages until such time as it is desired to cause such rupture to occur.

For some applications and with some reactant materials, the resulting product mixture can be used as such whereas, in other circumstances, it will be desirable to separate the desired product from the product mixture. With other starting materials, it will be possible to control the condensation reaction conditions to favour the production of the desired mixed hydrophilic/lipophilic product.

Other features of the invention and the advantages presented thereby will become apparent as the description herein proceeds.

The invention will now be further described by way of illustration in the following Examples:

EXAMPLE 1

Stearyl alcohol in the amount of 27.0 gms was mixed with 5.8 gm of glyoxal and 89 gm of a water-soluble oxyethylated alcohol obtained by treating methanol with six moles of ethylene oxide. The pH value of the resulting liquid mixture was then adjusted to a value of 3.0 by the dropwise addition of concentrated hydrochloric acid and the mixture was subsequently heated for one hour with continuous agitation at a temperature of 70°–75° C. To the reaction mixture, there were then added 50 ml of benzene and the water formed during the acetal formation reaction was removed by azeotropic distillation. After 14 gm of water had been removed, the reaction mixture was cooled to room temperature and was then carefully adjusted to a pH of 9.5–10.5 by the dropwise addition of a 50% aqueous solution of sodium hydroxide. The benzene solvent was then removed by evaporation under a reduced pressure of 10–20 mm Hg at 70° C., adding occasionally during the evaporation process small amounts of an aqueous solution of sodium hydroxide to maintain alkalinity. The final product was a viscous yellowish liquid.

It is believed that the following reactions take place:

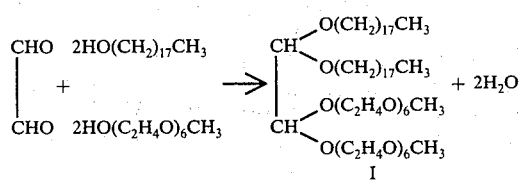

I

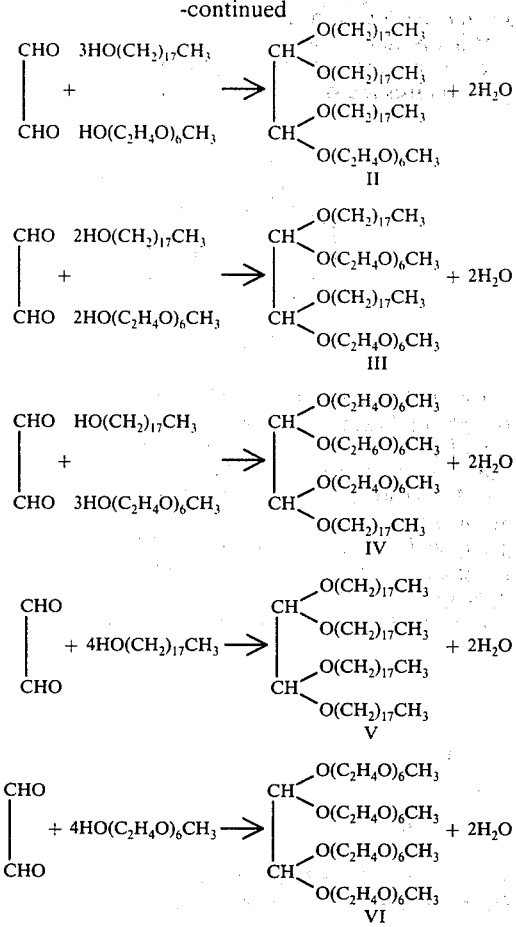

of the products obtained, those indicated at I, II, III and IV present the desired surface active property while the products indicated at V and VI are not significantly surface active. The product mixture obtained did, however, show the desirable properties provided in accordance with this invention as will be understood by observation of the test results set down below.

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 31.5 dynes/cm at a pH of 11.0. After the addition of 4.3 ml of 10% hydrochloric acid to 20 ml of that 10% aqueous solution, the surface tension of the resulting mixture increased to a value of 47.2 dynes/cm at the prevailing pH of 3.8.

EXAMPLE 2

Stearyl alcohol in the amount of 27.0 gm was mixed with 5.8 gm of glyoxal and 49.2 gm of a water-soluble oxyethylated alcohol obtained by treating methanol with three moles of ethylene oxide. The pH value of the resulting liquid mixture was then adjusted to a value of 3.0 by the dropwise addition of concentrated hydrochloric acid and the mixture was then heated for one hour with continuous agitation at a temperature of 70°-75° C. To the reaction mixture, there were then added 50 ml of benzene and the water formed during the acetal formation reaction was removed by azeotropic distillation. After 14 gm of water had been removed, the reaction mixture was cooled to room temperature and was then carefully adjusted to a pH of 9.5-10.5 by the dropwise addition of 50% aqueous solution of sodium hydroxide. The benzene solvent was then removed by evaporation under a reduced pressure of 10-20 mm at 70° C., adding occasionally during the evaporation process small amounts of an aqueous solution of sodium hydroxide to maintain alkalinity. The final product was a viscous yellowish liquid.

It is believed that a mixture of products is obtained as was the case in Example 1. The product mixture which was obtained presented the properties indicated below.

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 34.6 dynes/cm at a pH of 11.0. After the addition of 2.7 ml of 10% hydrochloric acid to 20 ml of that 10% aqueous solution, the surface tension of the resulting mixture increased to a value of 48.2 dynes/cm at the prevailing pH of 3.8.

EXAMPLE 3

Terephthaldehyde in the amount of 13.4 gm was mixed with 27.0 gm of stearyl alcohol and 116 gm of a water-soluble oxyethylated derivative of morpholine obtained by treating that substance with ethylene oxide to obtain a mixture of products containing from 3 to 6 and averaging about 4.5 moles of ethylene oxide per molecule. The pH value of the resulting liquid mixture was then adjusted to a value of 3.0 by the dropwise addition of concentrated hydrochloric acid and the mixture was then heated for one hour with continuous agitation at a temperature of 70°-75° C. To the reaction mixture, there were then added 50 ml of benzene and the water formed during the acetal formation reaction was removed by azeotropic distillation. After 8 gm of water had been removed, the reaction mixture was cooled to room temperature and was then carefully adjusted to a pH of 9.5-10.5 by the dropwise addition of a 50% aqueous solution of sodium hydroxide. The benzene solvent was then removed by evaporation under a reduced pressure of 10-20 mm Hg at 70° C., adding occasionally during the evaporation process, small amounts of an aqueous solution of sodium hydroxide to maintain alkalinity. The final product was a viscous reddish liquid.

As was the case is Examples 1 and 2, it is believed that a mixture of reaction products is obtained, one of which will correspond to the following formula:

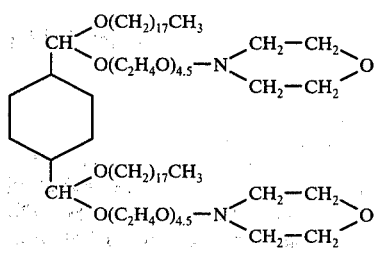

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 52.0 dynes/cm at a pH of 10.5. After the addition of 3.2 ml of 10% hydrochloric acid to 20 ml of that 10% aqueous solution, the surface tension of the resulting mixture increased to a value of 57.8 dynes/cm at the prevailing pH of 3.8.

EXAMPLE 4

Dodecanol in the amount of 18.6 gm was mixed with 5.8 gm of glyoxal and 49.2 gm of a water-soluble oxyethylated alcohol obtained by treating methanol with three moles of ethylene oxide per molecule. The pH value of the resulting liquid mixture was then adjusted to a value of 3.0 by the dropwise addition of concentrated hydrochloric acid and the mixture was then heated for one hour with continuous agitation at a temperature of 70°–75° C. To the reaction mixture, there were then added 50 ml of benzene and the water formed during the acetal formation reaction was removed by azeotropic distillation. After 14 gm of water had been removed, the reaction mixture was cooled to room temperature and was then carefully adjusted to a pH of 9.5–10.5 by the dropwise addition of a 50% aqueous solution of sodium hydroxide. The benzene solvent was then removed by evaporation under a reduced pressure of 10–20 mm Hg at 70° C., adding occasionally, during the evaporation process, small amounts of an aqueous solution of sodium hydroxide to maintain alkalinity. The final product was a viscous reddish liquid.

It is believed that a mixture of products is obtained as in several of the preceeding Examples; one of those products will have the formula:

$$CH \begin{matrix} O(CH_2)_{11}CH_3 \\ O(C_2H_4O)_3CH_3 \end{matrix}$$
$$CH \begin{matrix} O(CH_2)_{11}CH_3 \\ O(C_2H_4O)_3CH_3 \end{matrix}$$

A 1% aqueous solution of the mixed product formed a stable foam when shaken. Upon adjusting the pH value of this solution to 3.0 by the addition of hydrochloric acid, the foam disappeared and could not be regenerated by mechanical agitation.

A 10% aqueous solution of the product mixture exhibited a surface tension of 27.2 dynes/cm at a pH of 11.0. After the addition of 3.2 ml of 10% hydrochloric acid to 20 ml of that 10% aqueous solution, the surface tension of the resulting mixture increased to a value of 48.0 dynes/cm at the prevailing pH of 3.8.

EXAMPLE 5

An emulsion base was prepared by blending the following materials:
Acetal prepared as described in Example 2: 7.6 g
Potassium hydroxide: 1.5 g
Water: 0.6 g
Hexylene glycol: 1.0 g
"Sun Oil - 100 seconds"*: 5.6 g
*An oil conventionally used in the manufacture of cutting oil emulsions.

5 g of the emulsion base were then blended with 1 g of hexylene glycol and a further 5 g of Sun Oil - 100 seconds and the resulting blend was emulsified in 190 g of water.

On the addition of 10 ml concentrated hydrochloric acid to the emulsion, that emulsion immediately broke down and separated during a period of about 20 minutes into two clearly defined layers - an upper oily layer and an aqueous lower layer.

What is claimed is:

1. A surface active compound selected from the group consisting of wherein at least one of $R^2$, $R^3$, $R_5$ and $R^6$ is a lipophilic straight or branched chain hydrocarbon group having from 8 to 24 carbon atoms and at least one of $R^2$, $R^3$, $R^5$ and $R^6$ is a hydrophilic oxyalkylated group having from 1 to 24 oxyalkylene groups and having a terminal alkyl group of from 1 to 4 carbon atoms or a morpholine group and wherein $R^2$, $R^3$, $R^5$ and $R^6$ are selected from the group consisting of said lipophilic group and said hydrophilic oxyalkylated group.

2. The surface active compound of claim 1 having the formula $$C \begin{matrix} OR^2 \\ OR^3 \end{matrix}$$
$$C \begin{matrix} OR^5 \\ OR^6 \end{matrix}$$

wherein $R^2$, $R^3$, $R^5$ and $R^6$ represent groups selected from the class consisting of groups having the following formulae:

—$(C_2H_4O)_m$ $CH_3$ in which $m$ represents an integer from 3 to 6;
—$(CH_2)_{17}$ $CH_3$; and
—$(CH_2)_{11}$ $CH_3$.

3. The surface active compound of claim 1 having the formula wherein $R^2$, $R^3$, $R^5$ and $R^6$ represent groups selected from the class consisting of groups having the following formulae:

—$(CH_2)_{17}$ $CH_3$ and $$-(C_2H_4O)_m-N \begin{matrix} CH_2-CH_2 \\ CH_2-CH_2 \end{matrix} O$$

in which $m$ represents an integer from 3 to 6.

4. A surface active compound of claim 1 wherein said oxyalkylated group has the formula $(C_2H_4O)_n$ wherein $n$ is an integer of from 1 to 24.

* * * * *

UNITED STATES PATENT AND TRADEMARK OFFICE
CERTIFICATE OF CORRECTION

PATENT NO. : 4,118,565

DATED : October 3, 1978

INVENTOR(S) : Gerhard Wolfgang Helmut Scherf

It is certified that error appears in the above-identified patent and that said Letters Patent are hereby corrected as shown below:

Claim 1, Col. 8, l. 16 - "$R_5$" should be -- $R^5$ --

Claim 4, Col. 8, l. 66 - "$(C_2H_4O)_n$" should be -- $(C_2H_4O)_n$ --

Signed and Sealed this

Fourteenth Day of August 1979

[SEAL]

Attest:

LUTRELLE F. PARKER

*Attesting Officer*   *Acting Commissioner of Patents and Trademarks*